June 24, 1958 E. S. BOERNER Plant Pat. 1,720
ROSE PLANT
Filed Oct. 28, 1957
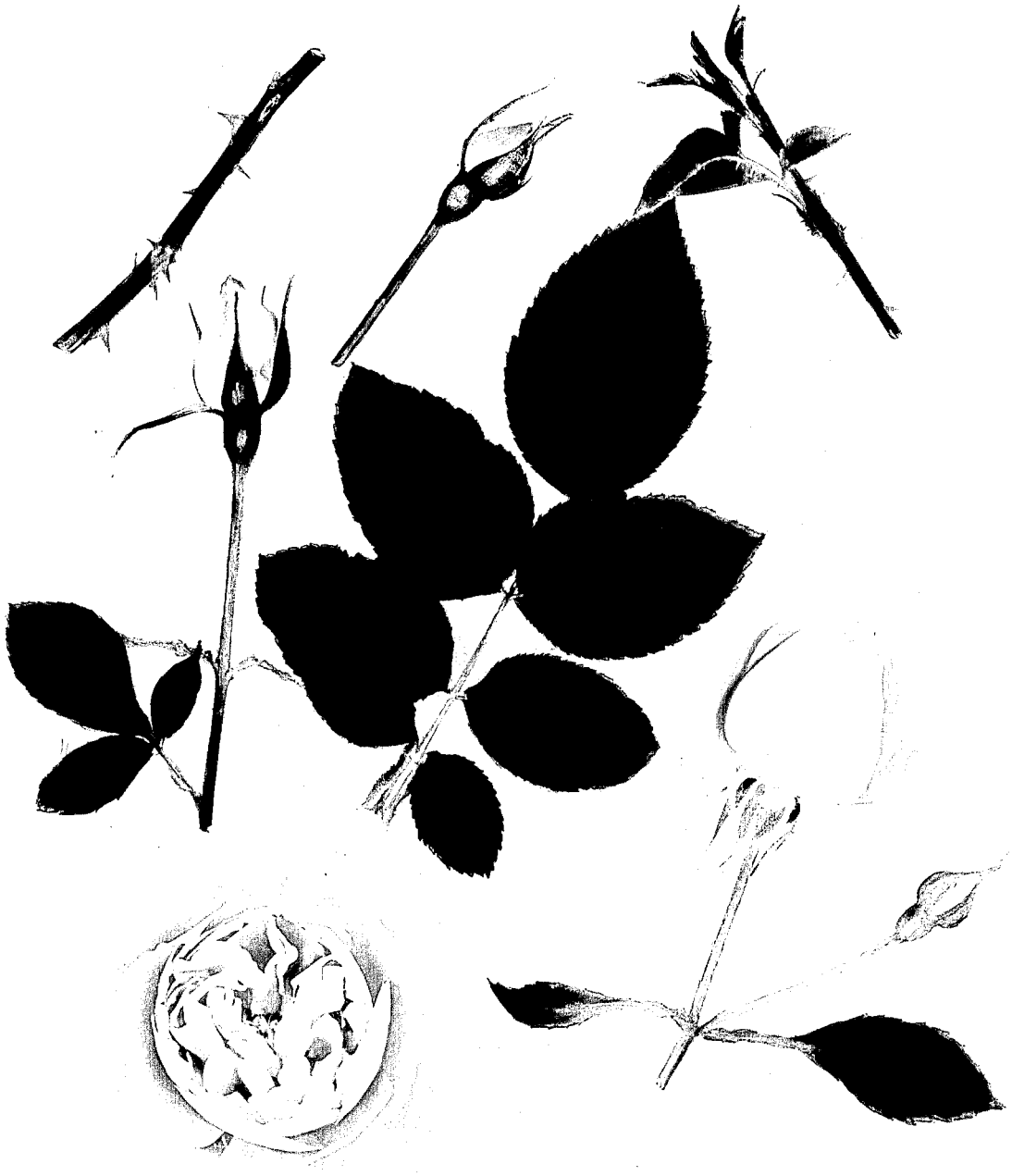
Inventor.
E. S. Boerner
By: Robb & Robb
Attorneys.

United States Patent Office

Plant Pat. 1,720
Patented June 24, 1958

1,720

ROSE PLANT

Eugene S. Boerner, Newark, N. Y., assignor to Jackson & Perkins Company, Newark, N. Y., a corporation of New York Application October 28, 1957, Serial No. 692,992

1 Claim. (Cl. 47—61)

The present invention relates to a new and distinct variety of rose plant of the large-flowered polyantha class, which was originated by me by crossing an unnamed and unpatented floribunda seeding of "Lavender Pinocchio" (Plant Patent No. 947) with the variety "Grey Pearl" (Plant Patent No. 680).

The primary objective of this breeding was to produce a new rose variety of the large-flowered polyantha class which bears flowers of a color or combination of colors that is new in the rose world and distinctly different from the flower color of such well-known varieties as "Twilight" (Plant Patent No. 1,484), "Lavender Pinocchio' (Plant Patent No. 947) and "Amy Vanderbilt" (Plant Patent No. 1,585). This objective was fully achieved, along with other improvements, as evidenced by the following characteristics which are outstanding in the new variety and distinguish it from its parents, as well as from all other varieties of its class of which I am aware:

(1) The floribunda type flowers which are borne individually, several together and also in clusters;

(2) The distinctive color of the buds which may be briefly described as Rufous in general color tonality, with the outer edges of the petals lightly overcast with Eosine Pink, which gives almost a brown effect to the buds; and (3) The distinctive color of the open flowers which may be briefly described as light Ochraceous Salmon, with the upper half of the petals lightly overcast with Pinkish Vinaceous, and with the margins of the petals edged with Thulite Pink, these colors as a whole being brightened by the colors of the reverse of the flower petals which are Straw Yellow in general color tonality, with the lower half of the petals overcast with Empire Yellow.

Asexual reproduction of the new variety by budding, as performed at Newark, New York, and also at Pleasonton, California, shows that the foregoing characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed floribunda seedling of "Lavender Pinocchio."

*Pollen parent.*—"Grey Pearl."

Classification:

*Botanic.*—Large-flowered polyantha.

*Commercial.*—Floribunda.

*Flower*

(Observations made from specimens grown in a greenhouse at Newark, New York, in the early morning and in the latter part of the month of March.)

Blooming habit: Recurrent—continuous.

Bud:

*Size.*—Large.

*Form.*—Ovoid; is not affected by wet or hot weather.

*Color.*—When sepals first divide—Carmine, Plate 1, with lower half of petal lightly overcast with Pinard Yellow, Plate 4. When petals begin to unfurl—Empire Yellow, Plate 4, faintly overcast with Spectrum Red, Plate 1. When half-blown: inside of petals—Rufous, Plate 14, with outer edges of petals lightly overcast with Eosine Pink, Plate 1; reverse of petals—Apricot Yellow, Plate 4, with outer edges of petals faintly overcast with Eosine Pink, Plate 1.

*Sepals.*—Slightly branched; curl back when petals begin to unfurl. Color: inside—Absinthe Green, Plate 31; outside—Rinnemann's Green, Plate 18.

*Calyx.*—Color—Rinnemann's Green, Plate 18. Shape—pear. Size—small. Aspect—smooth. Odor when rubbed—none.

*Peduncle.*—Length—medium. Aspect—rough. Strength—erect; heavy. Color—Biscay Green, Plate 17.

*Opening.*—Opens up well; is not affected by adverse weather conditions.

Bloom:

*Size.*—Medium. Average size when fully expanded—from 3½ to 4 inches.

*Borne.*—Some singly; some several together; some in clusters.

*Stems.*—Medium length; strong.

*Form (when first open).*—Cupped. Permanence—retains its form to the end, but outer petals curl back.

*Petalage.*—Double (full but open center). Number of petals under normal conditions—from 35 to 40.

*Color.*—Center of flower—Light Ochraceous Salmon, Plate 15, with petal edges lightly overcast with Eosine Pink, Plate 1. Outer petals—lower quarter of petal Pinard Yellow, Plate 4, with upper half of petal overcast with Flesh Color, Plate 14, and with outer edges of petal flushed with Thulite Pink, Plate 26. Base of petals (aiglet)—Light Cadmium, Plate 14. Inside of petals—Light Ochraceous-Salmon, Plate 15, with upper half of petal lightly overcast with Pinkish Vinaceous, Plate 27, and with edges of petals Thulite Pink, Plate 26. Reverse of petals—Straw Yellow, Plate 16, with lower half of petal overcast with Empire Yellow, Plate 4.

*General tonality from a distance.*—Light Ochraceous-Salmon, Plate 15, with edges of petals lightly overcast with Eosine Pink, Plate 1.

*Discoloration.*—General tonality at end of first day—Light Ochraceous-Salmon, Plate 15, with edges of petals lightly overcast with Eosine Pink, Plate 1. Second day—Light Ochraceous-Salmon, Plate 15, with edges of petals overcast with Thulite Pink, Plate 26. Third day—Flesh color, Plate 14, with outer edge of petals overcast with Thulite Pink, Plate 26.

Petals:

*Texture.*—Thick; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; small.

*Persistence.*—Drop off cleanly.

*Fragrance.*—Strong. Nature—"Old Rose perfume" (centifolia).

*Lasting quality.*—On the plant—long. As cut flower—long.

*Genital organs*

Stamens, anthers: Large; many; regularly arranged around styles. Color—Light Orange-Yellow, Plate 3.

Stamens, filaments (threads): Medium length. Color—Spectrum Red, Plate 1.

Pollen: Color—Buff Yellow, Plate 4.

Styles: Bunched; uneven length; medium length; thin.

Stigmas: Color—Picric Yellow, Plate 4.

Ovaries: All enclosed in calyx.

Hips: None.

Seeds: None.

*Plant*

Form: Bush.

Growth: Vigorous; upright.

Foliage: Compound of 5 to 7 leaflets.

*Size.*—Medium.

*Quantity.*—Normal.

*Color.*—New foliage: upper side—Bordeaux, Plate 12; under side—Deep Dull Yellow-Green (1), Plate 32, lightly overcast with Bordeaux, Plate 12. Old foliage: upper side—Forest Green, Plate 17; under side—Light Cress Green, Plate 31.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Absinthe Green, Plate 31. Under side—prickly.

*Stipules.*—Medium length; bearded.

Wood:

*New wood.*—Color—Yellowish Oil Green, Plate 5, lightly overcast with Bordeaux, Plate 12. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its habit of bearing flowers individually, several together and in clusters, the distinctive Rufous general color tonality of its buds whose petals have their outer edges lightly overcast with Eosine Pink and giving the buds a substantially brown effect, and the distinctive color of its open flowers of light Ochraceous-Salmon general color tonality, with the upper half of the flower petals lightly overcast with Pinkish Vinaceous and with the margins of the petals edged with Thulite Pink, while the reverse of the petals is Straw Yellow in general color tonality, with the lower half of the petals overcast with Empire Yellow and brightening the flower color as a whole.

No references cited.